United States Patent
Ohishi

(10) Patent No.: US 10,937,226 B2
(45) Date of Patent: Mar. 2, 2021

(54) MEDICAL IMAGE PROCESSING APPARATUS, RECONSTRUCTION METHOD AND X-RAY DIAGNOSTIC APPARATUS BASED ON A CHANGE OF A DENSITY OF A CONTRAST AGENT OVER TIME

(71) Applicant: CANON MEDICAL SYSTEMS CORPORATION, Otawara (JP)

(72) Inventor: Satoru Ohishi, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 193 days.

(21) Appl. No.: 15/918,497

(22) Filed: Mar. 12, 2018

(65) Prior Publication Data
US 2018/0260998 A1 Sep. 13, 2018

(30) Foreign Application Priority Data
Mar. 13, 2017 (JP) .............................. JP2017-047808

(51) Int. Cl.
*G06T 15/08* (2011.01)
*A61B 6/00* (2006.01)
*G06T 7/00* (2017.01)

(52) U.S. Cl.
CPC .............. *G06T 15/08* (2013.01); *A61B 6/481* (2013.01); *A61B 6/504* (2013.01); *A61B 6/5205* (2013.01); *A61B 6/5217* (2013.01); *G06T 7/0014* (2013.01); *G06T 7/0016* (2013.01);

(Continued)

(58) Field of Classification Search
None
See application file for complete search history.

(56) References Cited

U.S. PATENT DOCUMENTS 10,575,811 B2* 3/2020 Ohishi ................. A61B 6/4441
2005/0185831 A1* 8/2005 Rasche ..................... G06T 7/60
382/133

(Continued)

FOREIGN PATENT DOCUMENTS

JP 2004-201730 A 7/2004
JP 2010-12097 1/2010

(Continued)

OTHER PUBLICATIONS

Japanese Office Action dated Dec. 22, 2020, issued in Japanese Patent Application No. 2017-047808.

*Primary Examiner* — Tahmina N Ansari
(74) *Attorney, Agent, or Firm* — Oblon, McClelland, Maier & Neustadt, L.L.P.

(57) ABSTRACT

A medical image processing apparatus comprises processing circuitry configured to acquire a first blood vessel image based on X-rays that are irradiated from a first direction and a second blood vessel image based on X-rays that are irradiated from a second direction; determine a corresponding point on the second blood vessel image, which is a point corresponding to a subject point on the first blood vessel image, by using an epipolar line corresponding to the subject point and blood-flow information based on a change of a density of a contrast agent over time at the subject point; and reconstruct a three-dimensional blood vessel image by using information about the subject point and the corresponding point.

19 Claims, 7 Drawing Sheets

(52) U.S. Cl.
CPC ............... *G06T 2207/10116* (2013.01); *G06T 2207/30104* (2013.01); *G06T 2210/41* (2013.01)

(56) References Cited

U.S. PATENT DOCUMENTS

| | | | |
|---|---|---|---|
| 2006/0210147 A1* | 9/2006 | Sakaguchi | G01C 11/06 382/154 |
| 2008/0137934 A1* | 6/2008 | Sakaguchi | A61B 6/4441 382/132 |
| 2009/0016587 A1* | 1/2009 | Strobel | A61B 6/469 382/130 |
| 2016/0151034 A1* | 6/2016 | Ohishi | A61B 6/4266 378/98.12 |
| 2018/0260998 A1* | 9/2018 | Ohishi | G06T 15/08 |

FOREIGN PATENT DOCUMENTS

| | | |
|---|---|---|
| JP | 2015-29811 | 2/2015 |
| JP | 2016-101364 | 6/2016 |
| WO | WO 2014-162740 A1 | 10/2014 |

\* cited by examiner

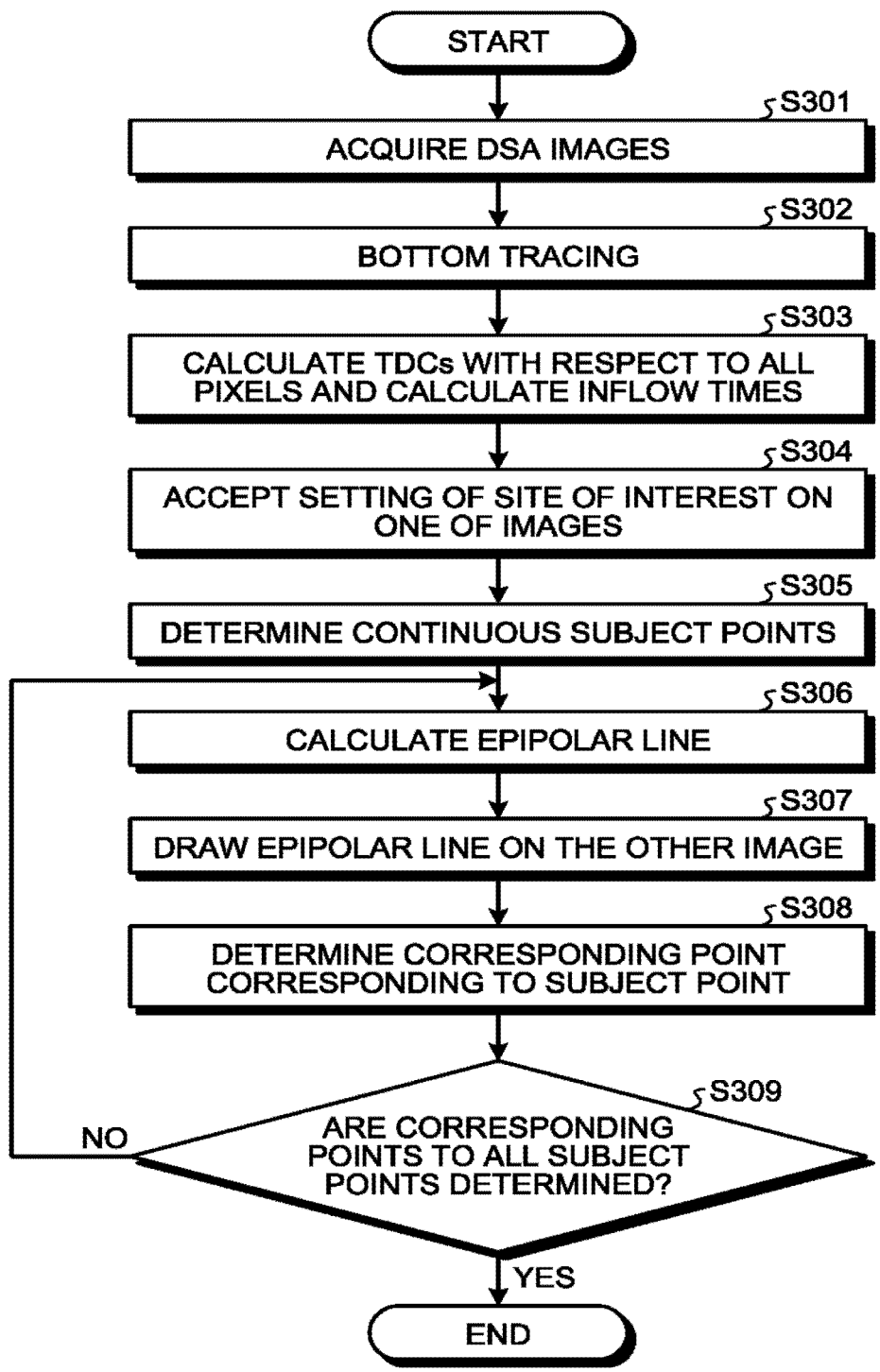

MEDICAL IMAGE PROCESSING APPARATUS, RECONSTRUCTION METHOD AND X-RAY DIAGNOSTIC APPARATUS BASED ON A CHANGE OF A DENSITY OF A CONTRAST AGENT OVER TIME

CROSS-REFERENCE TO RELATED APPLICATIONS

This application is based upon and claims the benefit of priority from Japanese Patent Application No. 2017-47808, filed on Mar. 13, 2017; the entire contents of which are incorporated herein by reference.

FIELD

Embodiments described herein relate generally to a medical image processing apparatus, a reconstruction method and an X-ray diagnostic apparatus.

BACKGROUND

Conventionally, there has been an X-ray diagnostic apparatus that includes a first imaging system and a second imaging system. Such X-ray diagnostic apparatuses are known for a method of, when generating a three-dimensional roadmap image, for example, simply reconstructing a three-dimensional blood vessel image from a DSA image imaged from the first imaging system and a DSA image imaged from the second imaging system.

BRIEF DESCRIPTION OF THE DRAWINGS

FIG. 8 is a flowchart illustrating an exemplary procedure of a correspondence relation determining process performed by an X-ray diagnostic apparatus according to a modification of the first embodiment.

DETAILED DESCRIPTION

A medical image processing apparatus comprises processing circuitry. The processing circuitry is configured to acquire a first blood vessel image based on X-rays that are irradiated from a first direction and a second blood vessel image based on X-rays that are irradiated from a second direction. And the processing circuitry is configured to determine a corresponding point on the second blood vessel image, which is a point corresponding to a subject point on the first blood vessel image, by using an epipolar line corresponding to the subject point and blood-flow information based on a change of a density of a contrast agent over time at the subject point. And the processing circuitry is configured to reconstruct a three-dimensional blood vessel image by using information about the subject point and the corresponding point.

The medical image processing apparatuses, a reconstruction method and an X-ray diagnostic apparatus according to embodiments will be described below with reference to the accompanying drawings. Embodiments are not limited to the following embodiments. The content of descriptions of one embodiment is similarly applicable to other embodiments in principle.

Figure 1:
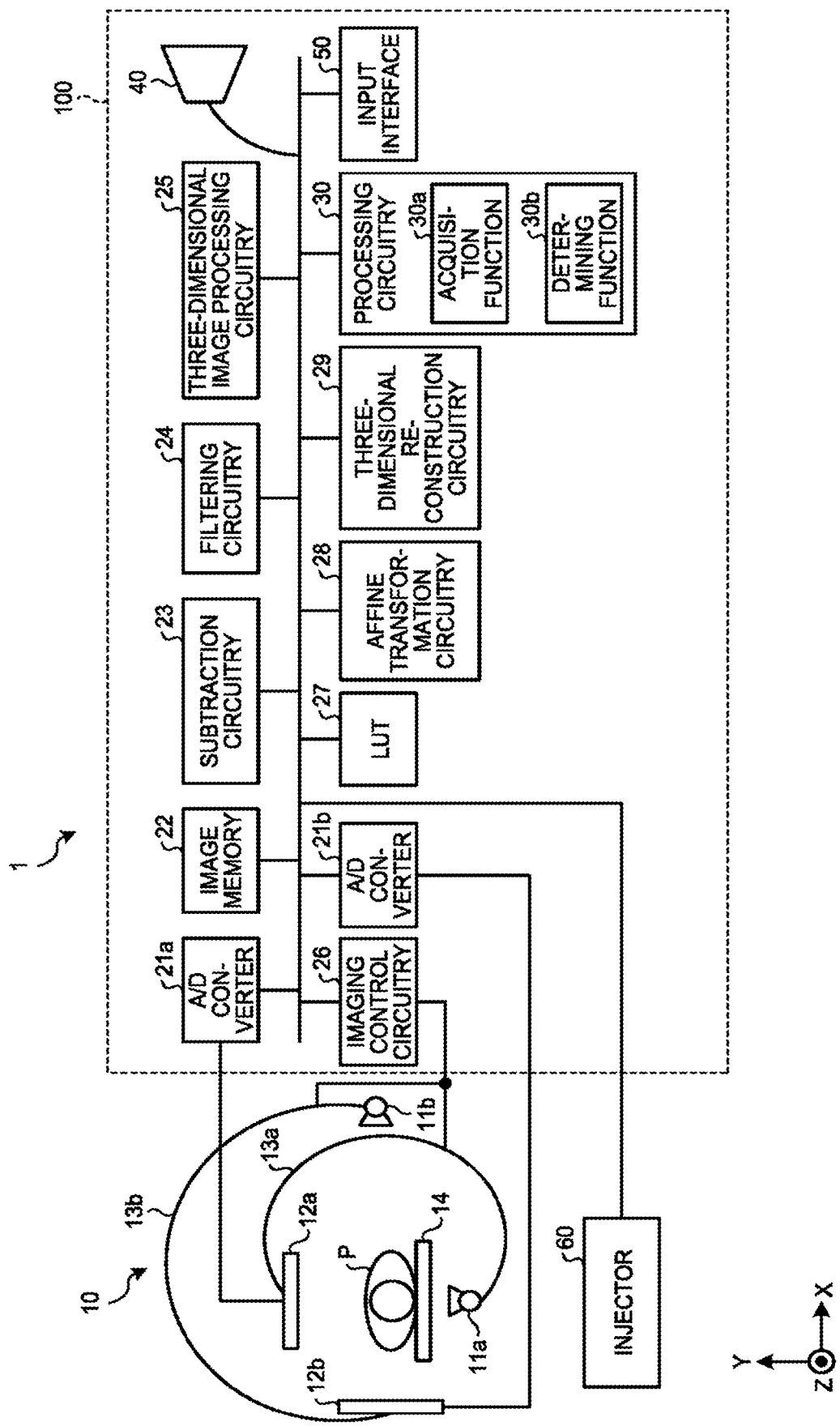
FIG. 1 is a block diagram illustrating an exemplary configuration of an X-ray diagnostic apparatus according to a first embodiment.

First of all, a configuration of an X-ray diagnostic apparatus according to a first embodiment will be described. FIG. 1 is a block diagram illustrating an exemplary configuration of an X-ray diagnostic apparatus 1 according to the first embodiment. The X-ray diagnostic apparatus 1 does not include a subject P (for example, a human body). The configuration illustrated in FIG. 1 is an example only. For example, each of the components exemplified in FIG. 1 may be configured in an integrated or separated manner.

As illustrated in FIG. 1, the X-ray diagnostic apparatus 1 according to the first embodiment includes an X-ray imaging mechanism 10 and a medical image processing apparatus 100. The X-ray imaging mechanism 10 is a biplane imaging mechanism that includes a first imaging system and a second imaging system. The first imaging system includes an X-ray tube 11a, an X-ray detector 12a and a C-arm 13a and the second imaging system includes an X-ray tube 11b, an X-ray detector 12b and an Ω-arm 13b.

The X-ray imaging mechanism 10 includes a tabletop 14, and an injector 60 is connected to the X-ray imaging mechanism 10. The tabletop 14 is a bed on which the subject P lies down. In the X-ray imaging mechanism 10, as illustrated in FIG. 1, a three-dimensional orthogonal coordinate system consisting of an X-axis, a Y-axis and a Z-axis is defined. In other words, the x-axis represents the horizontal direction, the Y-axis represents the vertical direction and the Z-axis represents a direction of the body axis of the subject P. In the three-dimensional orthogonal coordinate system, the directions indicated by the arrows serve as positive directions.

The X-ray tube 11a and the X-ray tube 11b are devices that generate X-rays by using a high voltage that is supplied from high-voltage generation circuitry (not illustrated in FIG. 1).

The X-ray detector 12a and the X-ray detector 12b are, for example, flat panel detectors (FPD) or image intensifiers (I.I.). The X-rev detector 12a and the X-ray detector 12b are devices in each of which X-ray detection elements for detecting X-rays passing through the subject P are arrayed in a matrix. Each of the X-ray detection elements converts X-rays having passed through the subject P into electric signals (X-ray signals), accumulates the electric signals, and stores the accumulated electric signals in an image memory 22, which will be described below.

The C-arm 13a is an arm that holds the X-ray tube 11a and the X-ray detector 12a. The X-ray tube 11a and the X-ray detector 12a are arranged by using the C-arm 13a such that the X-ray tube 11a and the X-ray detector 12a are opposed to each other with the subject P is between. The C-arm 13a supports the X-ray tube lie and the X-ray detector 12a and a motor that is provided on a supporter (not illustrated in FIG. 1) causes the C-arm 13a to rotate at a high speed around the subject P lying on the tabletop 14 as a propeller rotates. The C-arm 13a is supported rotatable on each of the three X, Y and Z axes that are orthogonal to one another and drive circuitry (not illustrated in FIG. 1) causes the C-arm 13a to rotate on each of the axes.

The Ω-arm 13b is an arm that holds the X-ray tube 11b and the X-ray detector 12b. The X-ray tube 11b and the X-ray detector 12b are arranged by using the C-arm 13b such that the X-ray tube 11b and the X-ray detector 12b are opposed to each other with the subject P in between. The C-arm 13b supports the X-ray tube 11b and the X-ray detector 12b and a motor that is provided on s supporter consisting of a ceiling rail (not illustrated in FIG. 1) causes the C-arm 13b to rotate around the subject P lying on the tabletop 14. The C-arm 13b is supported rotatably on each of the three X, Y and Z axes that are orthogonal to one another and the drive circuitry (not illustrated in FIG. 1) causes the Ω-arm 13b to rotate on each of the axes.

The injector 60 is a device for injecting a contrast agent from a catheter that is inserted into the subject P. The start of injection of the contrast agent from the injector 60 may be executed according to an injection start instruction that is received via the medical image processing apparatus 100, which will be described below, or may be executed according to an injection start instruction that is directly input by an operator to the injector 60. The X-ray imaging mechanism 10 configured as described above is controlled by imaging control circuitry 26, which will be described below.

As illustrated in FIG. 1, the medical image processing apparatus 100 includes an analog/digital (A/D) converter 21a, an A/D converter 21b, the image memory 22, subtraction circuitry 23, filtering circuitry 24, three-dimensional image processing circuitry 25, the imaging control circuitry 26, a look up table (LUT) 27, affine transformation circuitry 28, three-dimensional reconstruction circuitry 29, processing circuitry 30, a monitor 40 and an input interface 50.

The input interface 50 is, for example, a mouse and a keyboard, a trackball, or a pointing device, and the input interface 50 accepts various operations on the X-ray diagnostic apparatus 1. The monitor 40 displays various images that are processed by the medical image processing apparatus 100 and various types of information, such as a graphical user interface (GUI). For example, the monitor 40 is a cathode ray tube (CRT) monitor or a liquid crystal monitor.

For example, the input interface 50 includes an X-ray trigger button for instructing to irradiate X-rays. When the operator presses the X-ray trigger button, the X-ray diagnostic apparatus 1 starts imaging X-ray image data.

Under the control of the processing circuitry 30, the imaging control circuitry 26 controls various types of processing relating to imaging performed by the X-ray imaging mechanism 10. For example, by controlling the drive circuitry (not illustrated in FIG. 1), the imaging control circuitry 26 controls rotational imaging to acquire projection data at a given frame rate while rotating the C-arm 13a and the Ω-arm 13b. For example, in response to a signal that is output form the injector 60 when injection of the contrast agent is started, the imaging control circuitry 26 controls rotational imaging performed for multiple times after single injection of the contrast agent. While rotating and controlling the C-arm 13a and the Ω-arm 13b, the imaging control circuitry 26 controls the high-voltage generation circuitry (not illustrated in FIG. 1) to successively or intermittently generate X-rays from the X-ray tube 11a and the X-ray tube 11b and controls the X-ray detector 12a or the X-ray detector 12b to detect the X-rays having passed through the subject P. The imaging control circuitry 26 further controls imaging to acquire projection data at a given frame rate without rotating the C-arm 13a and the Ω-arm 13b.

The A/D converter 21a is connected to the X-ray detector 12a and converts analog signals that are input from the X-ray detector 12a into digital signals and stores the converted digital signals in the image memory 22 as an X-ray acquisition image. The A/D converter 21b is connected to the X-ray detector 12b and converts analog signals that are input from the X-ray detector 12b into digital signals and stores the converted digital signals in the image memory 22 as an X-ray acquisition image.

The image memory 22 stores X-ray acquisition images (projection data). For example, the image memory 22 stores each of projection data that is acquired by the first imaging system and projection data that is acquired by the second imaging system. The image memory 22 stores reconstruction data (volume data) that is reconstructed by the three-dimensional reconstruction circuitry 29, which will be described below, and a three-dimensional image that is generated by the three-dimensional image processing circuitry 25. The image memory 22 stores blood vessel images. For example, the image memory 22 stores subtraction images that are generated by the subtraction circuitry 23, which will be described below.

The subtraction circuitry 2 generates subtraction images, such as digital subtraction angiography (DSA) images. For example, the subtraction circuitry 23 generates subtraction images each between an acquisition image that is generated from X-ray signals that are acquired by imaging the subject without the existence of the contrast agent and an acquisition image that is generated from X-ray signals acquired by imaging the subject under the existence of the contrast agent. The former and latter acquisition images are referred to as a mask image and a contrast image, respectively. More specifically, the subtraction circuitry 23 generates a DSA image by using projection data of the mask image and the contrast image that are acquired approximately in the same direction and that are stored in the image memory 22. The subtraction circuitry 23 generates a first subtraction image based on X-rays irradiated by the first imaging system from a first direction and a second subtraction image based on X-rays irradiated by the second imaging system from a second direction.

The filtering circuitry 24 performs high-frequency enhancement filtering, etc. The LUT 27 performs gray scale conversion. The affine transformation circuitry 28 increases or reduces the size of an image and moves the image.

The three-dimensional reconstruction circuitry 29 reconstructs reconstruction data (hereinafter, referred to as three-dimensional image data or volume data) from the projection data that is acquired by the X-ray imaging mechanism 10. For example, using, as projection data, a subtraction image after subtraction that is obtained by the subtraction circuitry 23 by performing subtraction between a mask image and a contrast image and that is stored in the image memory 22, the three-dimensional reconstruction circuitry 29 reconstructs volume data from the projection data. Alternatively, using, as sets of projection data, a mask image and a contrast image that are obtained by conversion into digital data by the A/D converter 21a or the A/D converter 21b and that are stored in the image memory 22, the three-dimensional reconstruction circuitry 29 reconstructs sets of volume data from the sets of projection data. The subtraction circuitry 23 then performs a difference operation on the reconstructed two sets of volume data. The subtraction circuitry 23 stores the volume data obtained by the subtraction in the image memory 22.

The three-dimensional reconstruction circuitry 29 according to the first embodiment reconstructs volume data by using a subtraction image generated by the subtraction circuitry 23 on the basis of a mask image and a contrast image that are acquired by the first imaging system and a subtraction image generated by the subtraction circuitry 23 on the basis of a mask image and a contrast image that are acquired by the second imaging system. In other words, the three-dimensional reconstruction circuitry 29 reconstructs volume data by using two-dimensional X-ray images acquired from the two directions.

The three-dimensional image processing circuitry 25 generates a three-dimensional image from the volume data that is stored in the image memory 22. For example, the three-dimensional image processing circuitry 25 generates a volume rendering image and a multi planar reconstruction (MPR) image from the volume data. The three-dimensional image processing circuitry 25 stores the generated three-dimensional image in the image memory 22.

The processing circuitry 30 controls the whole X-ray diagnostic apparatus 1. Specifically, the processing circuitry 30 controls various types of processing relating to imaging of X-ray image, image reconstruction, generation of a display image that are performed by the X-ray imaging mechanism 10, display of a display image on the monitor 40, etc. The processing circuitry 30 accepts setting of a region of interest and setting of a subject point from the operator.

As illustrated in FIG. 1, the processing circuitry 30 executes an acquisition function 30a and a determining function 30b. For example, each of the processing functions executed by the acquisition function 30a and the determining function 30b that are functional components of the processing circuitry 30 represented in FIG. 1 are stored in the image memory 22 in a form of programs executable by a computer. The processing circuitry 30 is a processor that implements the function corresponding to each of the programs by reading each of the programs from the image memory 22 and executing the program. In other words, the processing circuitry 30 having read each of the programs has each of the functions represented in the processing circuitry 30 in FIG. 1. The acquisition function 30a is also referred to as an acquirer and the determining function 30b is also referred to as a determiner.

The image memory 22 is, for example, a semiconductor memory device, such as a random access memory (RAM) or a flash memory, or a storage device, such as a hard disk or an optical disk. The subtraction circuitry 23, the filtering circuitry 24, the three-dimensional image processing circuitry 25, the imaging control circuitry 26, the LUT 27, the affine transformation circuitry 28, the three-dimensional reconstruction circuitry 29, and the processing circuitry 30 are, for example, an electronic circuit, such as a central processing unit (CPU) or a micro processing unit (MPU), or an integrated circuit, such as an application specific integrated circuit (ASIC) or a field programmable gate array (FPGA).

An exemplary configuration of the X-ray diagnostic apparatus 1 according to the first embodiment has been described above. For example, when endovascular treatment is carried out, the X-ray diagnostic apparatus 1 configured as described above generates a three-dimensional roadmap image and displays the three-dimensional roadmap image on the monitor 40. When generating a roadmap image, the X-ray diagnostic apparatus 1 may use a method of simply reconstructing a blood vessel from a first subtraction image and a second subtraction image based on an epipolar line serving as a constraint condition. When an epipolar line serves as a restraint condition, the X-ray diagnostic apparatus 1 associates a blood vessel in the first subtraction image and a blood vessel in the second subtraction image with each other.

Figure 2:
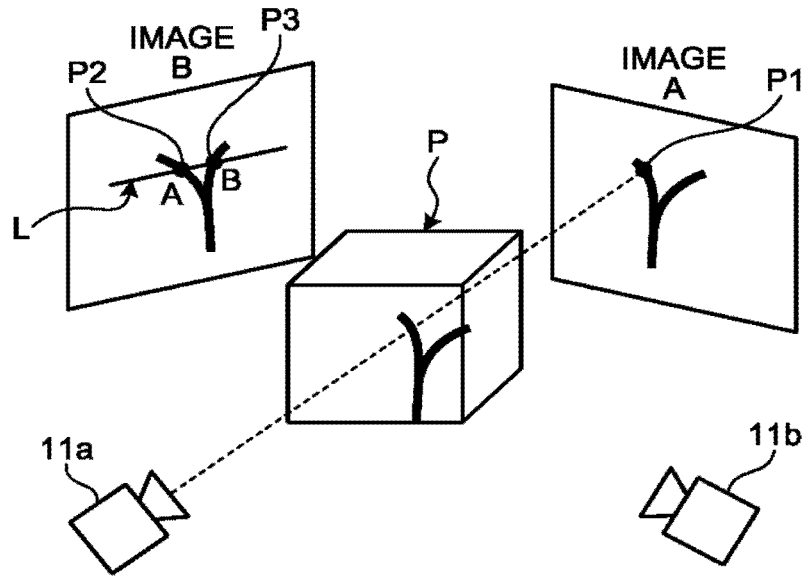
FIG. 2 is a diagram for explaining a conventional technology.

FIG. 2 is a diagram for explaining a conventional technology. FIG. 2 illustrates the case where a subject P is imaged from a first imaging system and a second imaging system. FIG. 2 represents a first subtraction image (an image A) based on X-rays irradiated from the X-ray tube 11a of the first imaging system and a second subtraction image (an image B) based on X-rays irradiated from the X-ray tube 11b of the second imaging system. When a subject point P1 is set in the image A, an epipolar line L based on the subject point on the image A is displayed on the image B. The epipolar line L is realized by the X-ray tube 11b by virtually projecting a straight line connecting a focal point of the X-ray tube 11a and the subject point P1 on the X-ray detector 12b. By using the epipolar line L, the X-ray diagnostic apparatus 1 determines a point on a blood vessel in the image B corresponding to the subject point P1 on a blood vessel in the image A.

As illustrated in the image B in FIG. 2, however, there is normally not only one blood vessel intersecting with the epipolar line L and there may be multiple blood vessels intersecting with the epipolar line L. More specifically, as illustrated in the image B in FIG. 2, the epipolar line L intersects with blood vessels at P2 and P3. For this reason, the conventional technology does not necessarily uniquely determine a blood vessel interesting with the epipolar line L in the image P. In such a case, in order to determine a point on a blood vessel in the image B corresponding to the subject point P1 on the blood vessel in the image A, manual operations by a specialist having knowledge about three-dimensional structures of blood vessels are necessary.

The X-ray diagnostic apparatus 1 according to the first embodiment thus executes a method of reconstructing a three-dimensional blood vessel image to be described below. The X-ray diagnostic apparatus 1 acquires, by performing difference processing between contrast images and non-contrast images that are generated over time in the first direction and the second direction, a first subtraction image based on X-rays irradiated from the first direction and a second subtraction image based on X-rays irradiated from the second direction. The X-ray diagnostic apparatus 1 then determines a corresponding point on the second subtraction image corresponding to the subject point on the first subtraction image by using an epipolar line and sets of blood-flow information about the subject point and the corresponding point. The X-ray diagnostic apparatus 1 then reconstructs a three-dimensional blood vessel image by using information about the subject point and the corresponding point.

Figure 3:
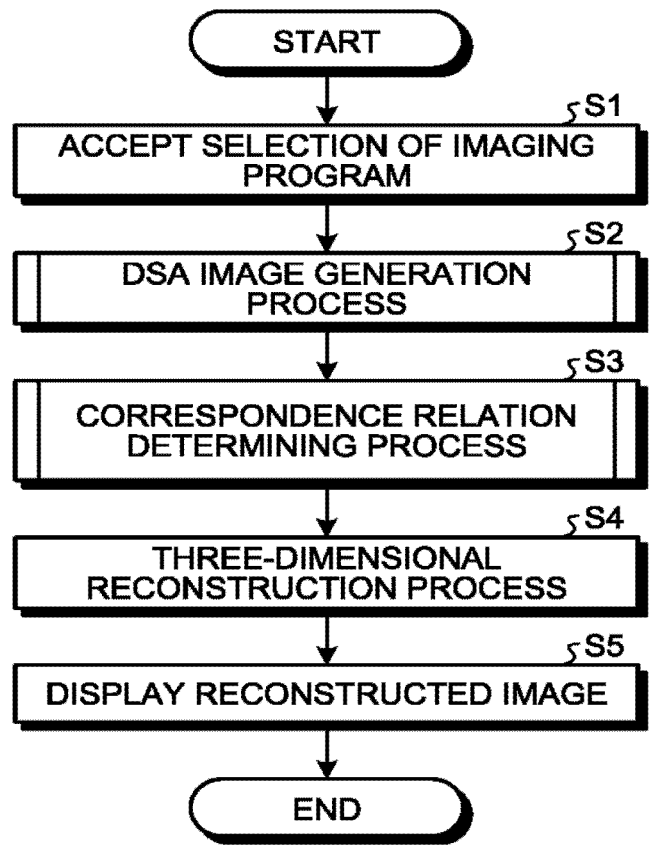
FIG. 3 is a flowchart illustrating an exemplary procedure of processes performed by the X-ray diagnostic apparatus according to the first embodiment.

An exemplary method of reconstructing a three-dimensional blood vessel image that is performed by the X-ray diagnostic apparatus 1 according to the first embodiment will be described below with reference to FIG. 3. FIG. 3 is a flowchart illustrating an exemplary procedure of processes performed by the X-ray diagnostic apparatus 1 according to the first embodiment. As illustrated in FIG. 3, the X-ray diagnostic apparatus 1 accepts selection of an imaging program (step S1). Step S1 is a step implemented by the processing circuitry 30. At step S1, the processing circuitry 30 accepts selection of a dedicated imaging program from the operator via the input interface 50. For example, the operator selects the dedicated imaging program when three-dimensional blood vessel information is required during angiographic examination or an intervention treatment.

In the imaging program, an angular interval between the first imaging system and the second imaging system during imaging is set in advance. The angular interval is set at 90 degrees normally. For example, when the C-arm 13a is set at an angle of (RAO0, CRA0), the Ω-arm 13b is set at (RAO90, CRA0). It is necessary to change the imaging direction according to the direction in which a blood vessel to be observed runs. For this reason, an imaging program may be prepared for each imaging direction. Alternatively, a GUI to determine an imaging direction may be provided and an imaging direction may be determined with the GUI during execution of the imaging program. For example, with a joystick, the direction in which the parallactic angle is set changes, without changing the angular interval, to the LAO direction when the joystick is leaned right, to the RAO direction when the joystick is leaned left, to the CRA direction when the joystick is leaned up, and to the CAU direction when the joystick is leaned down. Specifically, when the C-arm 13a is set at the angle (RAO0, CRA45) and the joystick is moved down, the positon at which the Ω-arm 13b is set is at the angle (RAO0, CAU45). At these angles, however, as the arms hit with each other, a function of moving the arms such that the arms are, without hitting with each other, as close as possible to the positions at which the arms are set may be used. For convenience of descriptions, the case where any one of the up-down and left-right directions is changed has been described; however, the embodiments are not limited thereto. In other words, a combination change of the imaging direction may be made by combining the up-down and left-right directions. For example, the upper direction and the rightward direction may be combined for a change or the upper direction and the leftward direction may be combined for a change. The downward direction and the rightward direction may be combined for a change or the downward direction and the leftward direction may be combined for a change.

The X-ray diagnostic apparatus 1 then executes a DSA image generation process (step 32). At step 32, the X-ray diagnostic apparatus 1 generates a first subtraction image and a second subtraction image. Details of the DSA image generation process at step S2 will be described with reference to FIG. 4 blow.

The X-ray diagnostic apparatus 1 executes a correspondence relation determining process (step S3). At step S3, the X-ray diagnostic apparatus 1 determines a corresponding point corresponding to a subject point that is set in the first subtraction image. Details of the correspondence relation determining process at step S3 will be described below with reference to FIG. 5.

The X-ray diagnostic apparatus 1 executes a three-dimensional reconstruction process (step S4). Step S4 is a step implemented by the three-dimensional reconstruction circuitry 29. At step S4, the three-dimensional reconstruction circuitry 29 reconstructs a three-dimensional blood vessel image by using information about the subject point and the corresponding point that are determined at step S3.

The X-ray diagnostic apparatus 1 displays the reconstructed image (step S5). Step S5 is a step implemented by the processing circuitry 30. At step S5, the processing circuitry 30 causes the monitor 40 to display the three-dimensional blood vessel image that is reconstructed at step S4.

Figure 4:
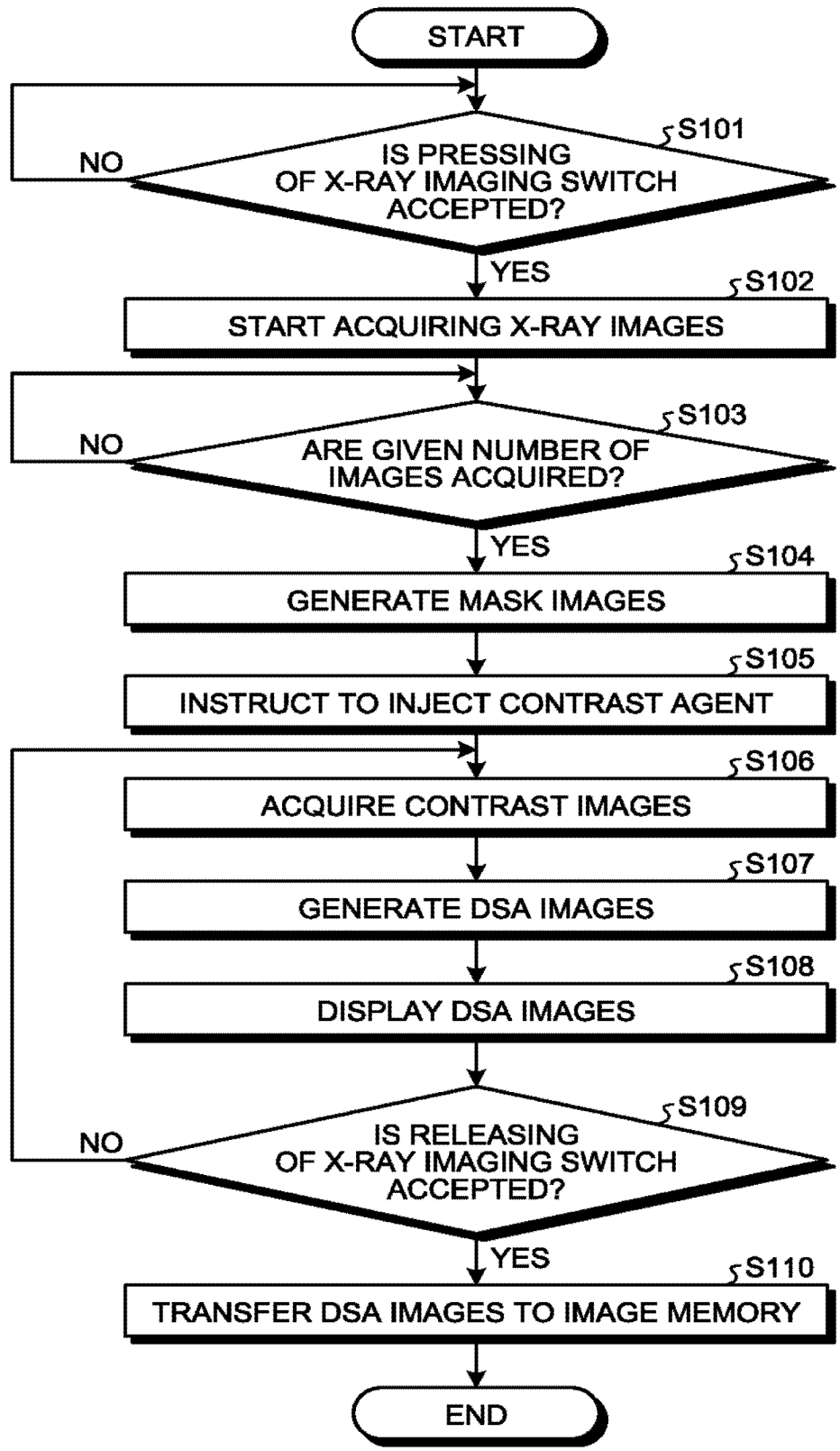
FIG. 4 is a flowchart illustrating an exemplary procedure of a DSA image generation process performed by the X-ray diagnostic apparatus according to the first embodiment.

The DSA image generation process will be described with reference to FIG. 4. FIG. 4 is a flowchart illustrating an exemplary procedure of the DSA image generation process performed by the X-ray diagnostic apparatus 1 according to the first embodiment. The DSA image generation process illustrated in FIG. 4 corresponds to step S2 in FIG. 3.

Step S101 illustrated in FIG. 4 is a step implemented by the processing circuitry 30. At step S101, the processing circuitry 30 determines whether pressing of an X-ray imaging switch is accepted. When it is not determined that pressing of the X-ray imaging switch is accepted (NO at step S101), the processing circuitry 30 repeats the determination process at step S101. On the other hand, when it is determined that pressing of the X-ray imaging switch is accepted (YES at step S101), the processing circuitry 30 causes the imaging control circuitry 26 to execute step S102. Before the start of step S101, it is preferable that a contrast agent is prepared in an injector to prepare for injection of the contrast agent.

Step S102 and step S103 are steps implemented by the imaging control circuitry 26. At step S102, the imaging control circuitry 26 starts acquiring X-ray images. For example, when the operator presses the X-ray imaging switch, the imaging control circuitry 26 controls the first imaging system and the second imaging system to start acquiring X-ray images. The imaging control circuitry 26 controls imaging to acquire projection data at a given frame rate without rotating the C-arm 13a and the Ω-arm 13b.

At step S103, the imaging control circuitry 26 determines whether a given number of images are acquired. The given number may be one or two or more. The given number varies depending on the noise level required for mask images. It is possible to set the given number in advance in the imaging program. When it is not determined that the given number of images are acquired (110 at step S103), the imaging control circuitry 26 repeats the determination process at step S103. On the other hand, when it is determined that the given number of images are acquired (YES at step S103), the imaging control circuitry 26 causes the subtraction circuitry 23 to execute step S104.

Step S104 is a step implemented by the subtraction circuitry 23. At step S104, the subtraction circuitry generates mask images. For example, the subtraction circuitry 23 averages the multiple images acquired at step S102 to generate a mask image with less noise. When the given number is one at step S102, the image acquired at step S102 may be used as a mask image and step S104 may be omitted.

Step S105 is a step implemented by the processing circuitry 30. At step S105, the processing circuitry 30 instructs to inject the contrast agent. For example, when the given number of images are acquired at step S103, the processing circuitry 30 instructs to start contrast enhancement to the operator, such as a person who performs an operation or provides treatment. For the instruction, an icon representing contrast enhancement may be displayed on the monitor 40 or an audio instruction may be made. Alternatively, a countdown for the timing of the start of contrast enhancement may be made on the monitor 40. Accordingly, when the timing is indicated, the operator starts injecting the contrast agent with an injector. Alternatively, after completion of acquisition of mask images, injection of the contrast agent may be started automatically with the injector 60.

Step S106 is a step implemented by the imaging control circuitry 26. At step S106, the imaging control circuitry 26 acquires contrast images. For example, on accepting the instruction to start injecting the contrast agent from the operator, the imaging control circuitry 26 controls the first imaging system and the second imaging system and starts X-ray imaging at a given frame rate. At step S106, the imaging control circuitry 26 controls imaging to acquire projection data at the given frame rate without rotating the C-ram 13a and the Ω-ram 13b. The given frame rate is, for example, 10 pps (pair per second). The frame rate is changed according to the blood flow rate in a subject blood vessel. For example, the frame rate is set at 30 pps for a site with a fast blood flow and at 6 pps for a site with a slow blood flow.

Step S107 is a step implemented by the subtraction circuitry 23. At step S107, the subtraction circuitry 23 generates DSA images. For example, the subtraction circuitry 23 generates a first subtraction image by performing subtraction on the contrast image and the mask image that are acquired by the first imaging system and generates a second subtraction image by performing subtraction on the contrast image and the mask image that are acquired by the second imaging system.

Step S108 and step S109 are steps implemented by the processing circuitry 30. At step S108, the processing circuitry 30 causes the monitor 40 to display the DSA images. When a subtraction image is generated at step S107, the processing circuitry 30 causes the monitor 40 to display the subtraction images approximately in real time.

At step S109, the processing circuitry 30 determines whether releasing of the X-ray imaging switch is accepted. When it is not determined that releasing of the X-ray imaging switch is accepted (NO at step S109), the processing circuitry 30 stoves to step S106. On the other hand, when it is determined that releasing of the X-ray imaging switch is accepted (YES at step S109), the processing circuitry 30 moves to step S110. For example, the operator releases the imaging switch after confirming contrast enhancement of a subject site while observing the DSA images displayed on the monitor 40.

Step S110 is a step implemented by the subtraction circuitry 23. At step S110, the subtraction circuitry 22 transfers the DSA images to the image memory 22. Each time a DSA image is generated, the subtraction circuitry 23 may transfer the DSA image to the image memory 22.

Figure 5:
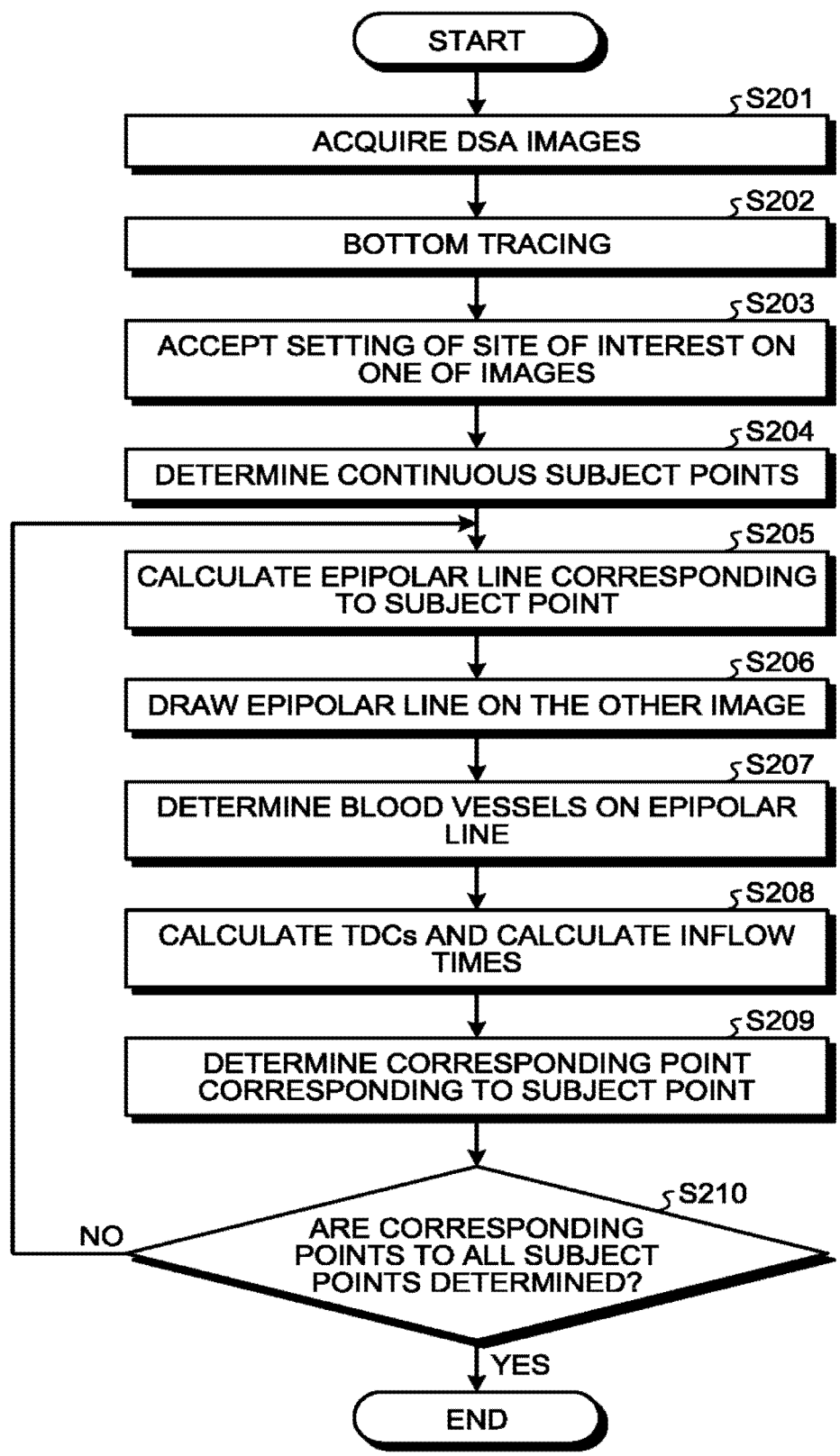
FIG. 5 is a flowchart illustrating an exemplary procedure of a correspondence relation determining process performed by the X-ray diagnostic apparatus according to the first embodiment.

With reference to FIG. 5, a correspondence relation determining process will be described. FIG. 5 is a flowchart illustrating an exemplary procedure of the correspondence relation determining process performed by the X-ray diagnostic apparatus 1 according to the first embodiment. The correspondence relation determining process illustrated in FIG. 5 corresponds to step S3 in FIG. 3.

Step S201 illustrated in FIG. 5 is a step corresponding to the acquisition function 30a. Step S201 is a step at which the acquisition function 30a is implemented by the processing circuitry 30 by loading a given program corresponding to the acquisition function 30a from the image memory 2 and executing the program. At step S201, the acquisition function 30a acquires DSA images. In other words, the acquisition function 30a acquires a first subtraction image based on the X-rays irradiated in the first direction and a second subtraction image based on the X-rays irradiated from the second direction, which are subtraction images each between a contrast image and a non-contrast image that are generated over time in the first direction and the second direction.

Steps S202 to S209 are steps corresponding to the determining function 30b. Steps S202 to S209 are steps at which the determining function 30b is realized by the processing circuitry 30 by loading a given program corresponding to the determining function 30b from the image memory 22 and executing the program. At steps S202 to S209, the determining function 30b determines a corresponding point on the second subtraction image corresponding to a subject point on the first subtraction image by using an epipolar line corresponding to the subject point and blood-flow information about the subject point. The determining function 30b calculates a blood inflow time as the blood-flow information. Details of steps S202 to S209 will be described below.

At step S202, the determining function 30b performs bottom tracing. For example, the determining function 30b performs bottom tracing on each of the first subtraction image and the second subtraction image. Bottom tracing is a process of extracting the minimum value of the intensity of transmitted X-rays per pixel as a representative pixel value of the pixel. Accordingly, blood vessels are extracted from the first subtraction image and the second subtraction image. The first subtraction image and the second subtraction image on which bottom tracing has been performed are transferred to the monitor 40 and, for example, the first subtraction image and the second subtraction image are displayed in parallel.

At step S203, the determining function 30b accepts setting of a site of interest on one of the images. For example, the determining function 30b accepts setting of a blood vessel of interest from the operator via the input interface 50 on any one of the first subtraction image and the second subtraction image on which bottom tracing has been performed. For example, the operator sets a bifurcation of blood vessels as blood vessels of interest. At step S204, the determining function 30b extracts a blood vessel in the site of interest and performs a thinning process on the extracted blood vessel, thereby determining the center line of the blood vessel as a set of continuous subject points. The image on which setting of the site of interest is accepted is also referred to also as a subject image. Furthermore, according to the following descriptions, setting of a blood vessel of interest is accepted on the first subtraction image on which bottom tracing has been performed.

At step S205, the determining function 30b calculates an epipolar line from the set of coordinates of the position of the subject point. At step S206, the determining function 30b draws the epipolar line on the other image. In other words, the determining function 30b determines, on the second subtraction image, the epipolar line corresponding to the subject point on the blood vessel that is specified on the first subtraction image. The image on which the epipolar line is drawn is also referred to as a corresponding image. At step S207, the determining function 30b determines sets of coordinates of the centers of blood vessels on the epipolar line as possible points. For example, the determining function 30b determines, as possible points, the centers of blood vessels each having a pixel value equal to or larger than a given threshold on the epipolar line.

At step S208, the determining function 30b calculates time-density curves (TDCs) of the subject point and the possible points from the DSA image and calculates inflow times. The inflow time is a parameter for which a change of the pixel value at each position in the DSA image data is regarded as a change of the density of the contrast agent and that is defined on the basis of the change of each pixel value over time. Note that any method may be selected as the method of calculating an inflow time. For example, it is possible to select, as the method of calculating an inflow time, the TTP (time-to-peak) that is a method of determining a time at which the change of the pixel value according to the time is the largest as an inflow time. Alternatively, for example, it is possible to select, as the method of calculating an inflow time, TTA (time-to-arrival) that is a method of determining, as an inflow time, a time at which the change of the pixel value over time reaches a given value or a time at which the ratio of the change of the pixel value over time to the maximum value reaches a given ratio.

Figure 6:
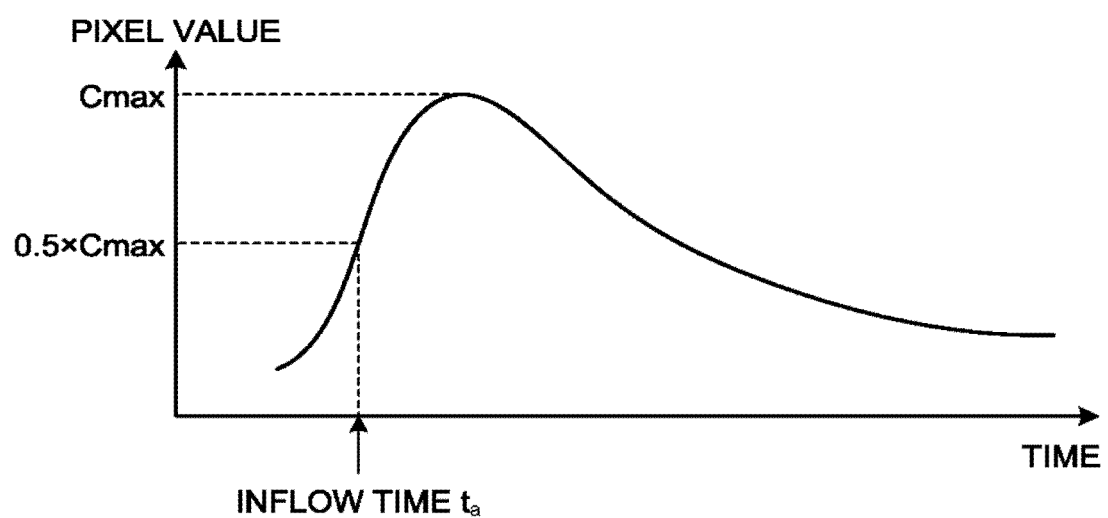
FIG. 6 is a first diagram for explaining the first embodiment.
Figure 7A:
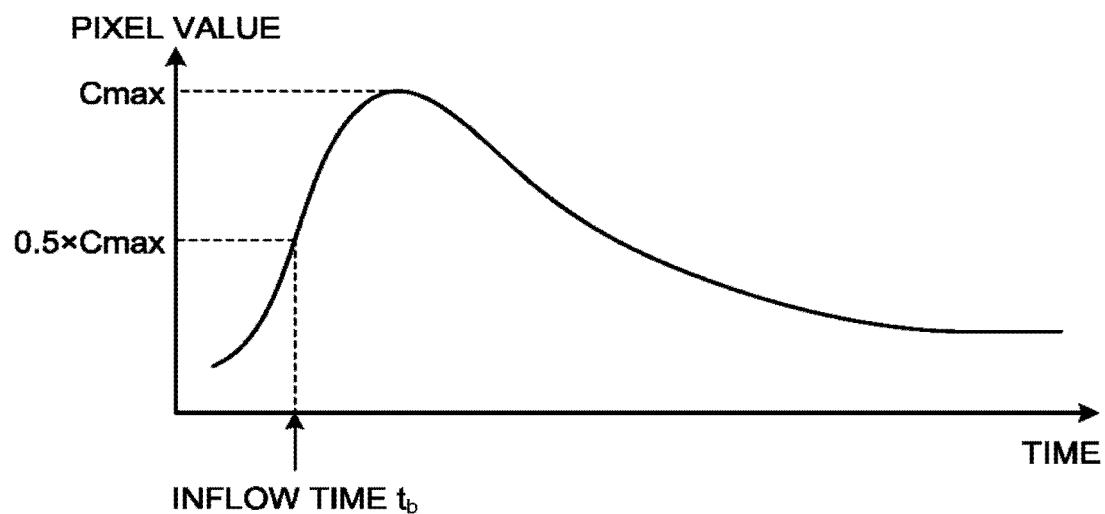
FIG. 7A is a second diagram for explaining the first embodiment.
Figure 7B:
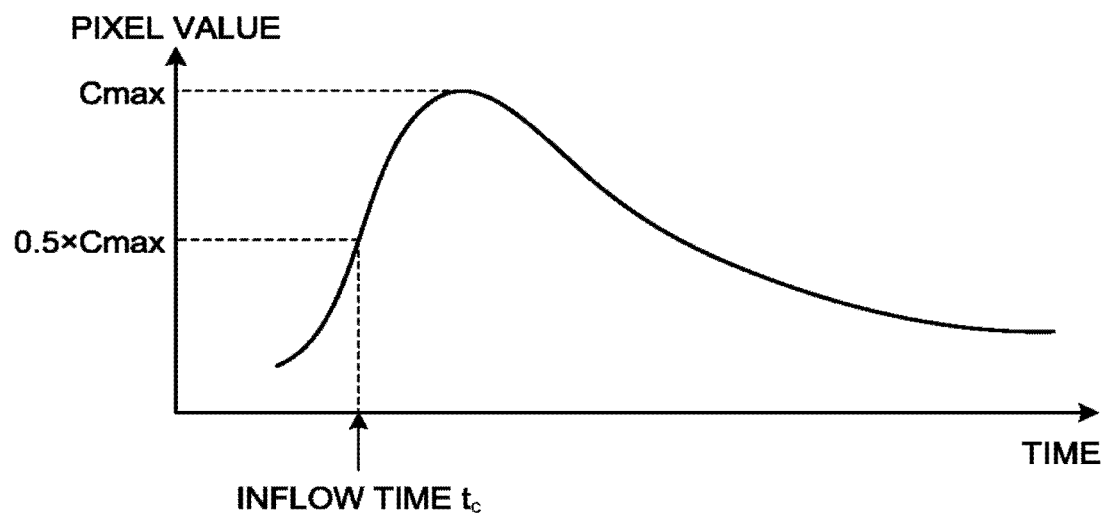
FIG. 7B is a third diagram for explaining the first embodiment.

FIG. 6 is a diagram for explaining the first embodiment. The horizontal axis in FIG. 6 represents the time and the vertical axis represents the pixel value. The example illustrated in FIG. 6 represents the case where the determining function 30b determines an inflow time by using ½ of the maximum value of the TDC as a threshold. The example illustrated in FIG. 6 represents the case where the inflow time with respect to the subject point is determined. The case where the inflow time with respect to the subject point P1 represented in FIG. 2 is determined will be described.

The determining function 30b determines an inflow time by analyzing a time density profile with respect to the pixel of the subject point P1 contained in the first subtraction image that is generated over time. In the example illustrated in FIG. 6, the determining function 30b calculates, as an inflow time, a time $t_a$ at which the pixel value reaches ½ of the maximum pixel value (Cmax) (0.5×Cmax).

In the same manner, the determining function 30b calculates a TDC of each possible point by analyzing the time density profile with respect to the pixel of each possible point contained in the second subtraction image that is generated over time and calculates an inflow time with respect to each possible point. For example, when N possible points are determined at step S207, the determining function 30b calculates TDCs of N possible points and calculates inflow times with respect to the N possible points. For convenience of description, it is assumed that the determining function 30b regards P2 and P3 as possible points and determines an inflow time $t_b$ with respect to P2 and an inflow time $t_c$ with respect to P3. Imaging by the first imaging system and imaging by the second imaging system do not occur concurrently. The same time is set for the time at which the first imaging system acquires the first frame and the time at which the second imaging system acquires the first frame and the first frames are displayed as ones acquired concurrently. Practically, however, acquisition by the first imaging system and the imaging by the second imaging system occur alternately. Specifically, in the case where imaging is performed at 10 pps, when the time at which the first imaging system acquires the first frame is 0, the time at which the second imaging system acquires the first frame is 50 msec. For this reason, in determining the inflow time $t_b$ with respect to P2 and the inflow time $t_c$ with respect to P3, it is necessary to determine inflow times in consideration of a delay between the imaging times.

At step S209, the determining function 30b determines a point corresponding to the subject point. In other words, the determining function 30b determines, on the blood vessel intersecting with the epipolar line, a corresponding point whose corresponding blood-flow information is similar to that about the subject point. For example, the determining function 30b compares ta, tb and tc and determines a possible point closest to ta as the corresponding point. On determining the corresponding point, the determining function 30b transmits the correspondence relation between the set of coordinates of the subject point and the set of coordinates of the corresponding point to the three-dimensional reconstruction circuitry 29.

At step S210, the determining function 30b determines whether corresponding points to all the subject points are determined. When it is not determined that corresponding points to all the subject points are determined (NO at step S210), the determining function 30b moves to step S250. In other words, the determining function 30b repeats the process from step S205 to step S209 along the blood vessel to determine the correspondence relation between the sets of coordinates of the subject points in the subject image and the sets of coordinates of the corresponding points in the corresponding image.

The three-dimensional reconstruction circuitry 29 reconstructs a three-dimensional blood vessel image by using the information about the subject point and the corresponding point. In other words, by using the information about the subject point and the corresponding point, the three-dimensional reconstruction circuitry 29 reconstructs a three-dimensional blood vessel image from the subtraction images that are generated over time in the first direction and the second direction. The three-dimensional reconstruction circuitry 29 determines the vascular center position as the intersect between the straight line connecting the focal point of the X-ray tube 11a and the subject point and the straight line connecting the focal point of the X-ray tube 11b and the corresponding point. Note that the two straight lines do not interest with each other in some cases. In that case, it points on the respective adjacent straight lines having the shortest distance in between are determined and the vascular center position can be calculated as the midpoint between the two points.

The three-dimensional reconstruction circuitry 29 corrects geometrical magnifying factor by X-rays with respect to the width of the blood vessel t the subject point and the corresponding point, determines the size of the blood vessel at the vascular center position, and reconstructs a three-dimensional cross section of the blood vessel having the determined size of the blood vessel at the determined vascular center position. The three-dimensional reconstruction circuitry 29 reconstructs a three-dimensional blood vessel by performing a process of reconstructing a vascular cross section along the site of interest. The three-dimensional reconstruction circuitry 29 transfers the reconstructed three-dimensional blood vessel as blood vessel information to the three-dimensional image processing circuitry 25.

The three-dimensional image processing circuitry 25 creates a three-dimensional blood vessel model by using the blood vessel information reconstructed by the three-dimensional reconstruction circuitry and causes the monitor 40 to display the three-dimensional blood vessel model. For example, the three-dimensional image processing circuitry 25 generates a three-dimensional blood vessel model like a continuous cylinder. More specifically, the three-dimensional image processing circuitry 25 generates a three-dimensional blood vessel model in which reconstructed ovals are continuously connected as vascular cross sections. The three-dimensional image processing circuitry 25 may display the created three-dimensional blood vessel model directly on the monitor 40 or synthesize the three-dimensional blood vessel model with the X-ray image that is generated in real time and the synthesized image may be displayed as a three-dimensional roadmap on the monitor 40.

As described above, in the first embodiment, after the possible points are determined by using the epipolar line corresponding to the subject point as the constraint condition, the blood-flow inflow time is determined from the concentration profile and one whose corresponding inflow time is closest to that about the subject point is determined as the corresponding point from among the possible points. In the first embodiment, performing the correspondence relation determining process sequentially along the site of interest enables reconstruction of the three-dimensional blood vessel information.

Accordingly, according to the first embodiment, it is possible to reconstruct simple three-dimensional blood vessel information from the DSA images that are generated over time in the first and second directions. As a result, the operator is able to easily use, for example, a three-dimensional roadmap during an operation or treatment.

In the above-described embodiment, the determining function 30b is described as one that accepts setting of blood vessel to be focused by the operator at step S203; however, the embodiments are not limited thereto. For example, the determining function 30b may select a given blood vessel site and set the site as a site of interest.

In the first embodiment, after the epipolar line corresponding to the subject point is used as the constraint condition and the possible points are determined, the blood-flow inflow time is further determined from the concentration profile and the one whose corresponding inflow time is closest to that of the subject point is determined as the corresponding point from among the possible points. Instead of determining the blood-flow inflow time, the TDC of the subject point may be compared with the TDCs of the possible points and one whose TDC is more close to that of the subject point among the possible points may be determined as the corresponding point.

The first embodiment describes the case where the determining function 30b determines, on the second subtraction image, the epipolar line corresponding to the subject point on the blood vessel that is specified on the first subtraction image and determines, on the blood vessel intersecting with the epipolar line, the corresponding point whose corresponding blood-flow information is similar to that about the subject point; however, the embodiments are not limited thereto. For example, the determining function 30b may determine possible points on the second subtraction image whose corresponding blood-flow information is similar to that about a subject point on the blood vessel that is specified on the first subtraction image and determine, as a corresponding point, a possible point intersecting with the epipolar line corresponding to the subject point from among the possible points.

FIG. 8 is a flowchart illustrating an exemplary procedure of the correspondence relation determining process performed by the X-ray diagnostic apparatus 1 according to a modification first embodiment. The correspondence relation determining process illustrated in FIG. 8 corresponds to step S3 in FIG. 3.

Step S301 illustrated in FIG. 8 is a step corresponding to the acquisition function 30a. Step S301 is a step at which the processing circuitry 30 loads the given program corresponding to the acquisition function 30a from the image memory 22 and executes the program and accordingly the acquisition function 30a is implemented. The process at step S301 is the same as the process at step S201 illustrated in FIG. 5. In other words, at step S301, the acquisition function 30a acquires DSA images.

Steps S302 to S308 are steps corresponding to the determining function 30b. Steps S302 to S308 are steps at which the processing circuitry 30 loads the given program corresponding to the determining function 30b from the image memory 22 and executes the program and accordingly the determining function 30b is implemented. The process at step S302 is the same as the process at step S202 illustrated in FIG. 5. In other words, at step S302, the determining function 30b performs bottom tracing.

At step S303, the determining function 30b calculates TDCs with respect to all the pixels and calculates inflow times. For example, the determining function 30b calculates blood-flow information about all the pixels in blood vessels on the first subtraction image and the second subtraction image.

The process at steps S304 to S306 is the same as the process at steps S203 to step S205. In other words, at step S304, the determining function 30b accepts setting of a site of interest on one of the images. At step S305, the determining function 30b extracts a blood vessel in the site of interest and performs the thinning process on the blood vessel, thereby determining a center line of the blood vessel as a set of continuous subject points. At step S306, the determining function 30b calculates an epipolar line from a set of coordinate of a subject point. At step S307, the determining function 30b draws the epipolar line on the other image.

At step S308, the determining function 30b determines a corresponding point corresponding to the subject point. The determining function 30b determines possible points on the second subtraction image whose corresponding blood-flow information is similar to that about the subject point that is determined on the blood vessel that is specified on the first subtraction image. The determining function 30b then determines, from among the possible points, a possible point intersecting with the epipolar line corresponding to the subject point as the corresponding point.

The process at step S309 is similar to the process at step S210 illustrated in FIG. 5. In other words, at step S308, the determining function 30b determines whether corresponding points to all the subject points are determined. When it is not determined that corresponding points to all the subject points are determined (NO at step S309), the determining function 30b moves to step S306. In other words, the determining function 30b repeats the process from step S306 to step S308 along the blood vessel to determine the correspondence relation between the sets of coordinates of the subject points in the subject image and the sets of coordinates of the corresponding points in the corresponding image.

As described above, in the modification of the first embodiment, a possible point whose corresponding blood-flow inflow time is similar to that of a subject point that is set on one of the images is determined from the other image and a possible point intersecting with an epipolar line corresponding to the subject point is determined as a corresponding point from among the possible points. Furthermore, in the modification of the first embodiment, performing the correspondence relation determining process sequentially along the site of interest enables reconstruction of three-dimensional blood vessel information.

Accordingly, according to the modification of the first embodiment, it is possible to reconstruct simple three-dimensional blood vessel information from DSA images that are generated over time in the first and second directions. As a result, the operator is able to easily use, for example, a three-dimensional roadmap during an operation or treatment.

According to the description of the above-described modification of the first embodiment, at step S303, the determining function 30b performs, as a pre-process, calculation of blood-flow information about all the pixels in blood vessels on the first subtraction image and the second subtraction image; however, the embodiments are not limited thereto. For example, the determining function 30b may perform, as a pre-process, calculation of blood-flow information about all the pixels in the blood vessel on the second subtraction image at step S303, accept setting of a site of interest, and then calculate blood-flow information about a subject point on the first subtraction image at step S304. Alternatively, at step S304, the determining function 30b may set a site of interest not only on one of the images but also on the other image and perform, as a pre-process, calculation of blood-flow information about only the sites of interest.

The first embodiment describes the case where setting of a site of interest is accepted from the operator; however, the embodiments are not limited thereto. A second embodiment describes the case where the X-ray diagnostic apparatus 1 sets a site of interest and determines a corresponding point. The whole configuration of the X-ray diagnostic apparatus 1 according to the second embodiment is the same as the exemplary configuration illustrated in FIG. 1 except for additional functions to the determining function 30b and the three-dimensional reconstruction circuitry 29 and thus descriptions thereof will be omitted herein.

The determining function 30b according to the second embodiment determines a set of subject points on a first subtraction image as a center line. For example, the determining function 30b performs bottom tracing on the first subtraction image and a second subtraction image and extracts blood vessels. The determining function 30b then performs the thinning process on the first subtraction image, from which the blood vessels are extracted, to determine the center lines of the blood vessels. By tracing the center lines, the determining function 30b determines the center lines as sets of subject points. The determining function 30b determines sets of coordinates of the respective determined subject points. The determining function 30b may further perform the thinning process on the second subtraction image, from which the blood vessels are extracted, to determine the center lines of the blood vessels and determine the center lines as sets of the subject points. Also in that case, the determining function 30b determines a set of coordinates of each of the determined subject points.

The determining function 30b determines each corresponding point on the second subtraction image corresponding to each of the subject points by using the epipolar line corresponding to each of the subject points and sets of blood-flow information about each of the subject points and each of the corresponding points. For example, the determining function 30b determines corresponding points by repeating the process at steps S205 to S209 illustrated in FIG. 5 with respect to each of the subject points. Alternatively, by repeating the process at step S306 to step S308 illustrated in FIG. 8 on each of the subject points, the determining function 30b determines corresponding points. Note that, when determining corresponding points according to the process procedure illustrated in FIG. 8, the determining function 30b executes step S303 illustrated in FIG. 8 in advance to calculate TDCs of all the pixels and calculate the inflow times.

As in the first embodiment and the modification of the first embodiment, the three-dimensional reconstruction circuitry 29 reconstructs a three-dimensional blood vessel image by using the information about each of the subject points and each of the corresponding points. The three-dimensional reconstruction circuitry 29 further reconstructs a three-dimensional center line by using the information about the subject points and the corresponding points.

As described above, in the second embodiment, a set of subject points on the first subtraction image is determined as a center line and corresponding points on the second subtraction image that correspond respectively to the subject points are determined by using epipolar lines corresponding respectively to the subject points and sets of blood-flow information each about each subject point and each corresponding point. Accordingly, according to the second embodiment, it is possible to reconstruct simple three-dimensional blood vessel information from DSA images that are generated over time in the first and second directions. As a result, the operator is able to easily use, for example, a three-dimensional roadmap during an operation or treatment.

The embodiments are not limited to the above-described embodiments.

According to the above-described embodiments, the determining function 30b uses information including only times and epipolar lines to determine corresponding points of a blood vessel. Alternatively, continuity of blood vessel may be used. In other words, the determining function 30b may further use continuity of blood vessel as a constraint condition to determine corresponding points. For example, the determining function 30b compares the inflow time with respect to a subject point with the inflow time with respect to each possible point and determines, as a corresponding point, a possible point whose corresponding inflow time is closest to that with respect to the subject point from among the possible points and that satisfies continuity of blood vessel. The continuity of blood vessel means that the blood vessel is continuous and thus there is no abrupt chance and thus the blood concentration does not change abruptly. More specifically, the determining function 30b calculates an inflow time in a blood vessel in the vicinity of a subject point in addition to an inflow time with respect to the subject point. The determining function 30b calculates, in addition to an inflow time with respect to each possible point, an inflow time with respect to a blood vessel in the vicinity of each possible point. The determining function 30b then determines, from among the possible points, a possible point for which the inflow time with respect to the possible point and the inflow time with respect to the vicinity of the possible points are similar to the inflow times with respect to the subject point and the vicinity of the subject point. Introducing the continuity of blood vessel complicates the calculation but improves the accuracy for the complicity.

The above-described embodiment describes the case where setting of a site of interest on the first subtraction image is accepted, the set of coordinates of the position of the center of the site of interest, which is set, is determined as the subject point and the epipolar line is drawn on the second subtraction image; however, the embodiments are not limited thereto. For example, setting of a site of interest on the second subtraction image may be accepted, a set of coordinates of the position of the center of the site of interest, which is set, may be determined as a subject point and an epipolar line may be drawn on the first subtraction image.

The above-described embodiment describes that the X-ray tube 11a, the X-ray detector 12a and the C-arm 13a serve as the first imaging system and the X-ray tube 11b, the X-ray detector 12b and the Ω-arm 13b serve as the second imaging system; however, the embodiments are not limited thereto. For example, the X-ray tube 11a, the X-ray detector 12a and the C-arm 13a may serve as the second imaging system and the X-ray tube 11b, the X-ray detector 12b and the Ω-arm 13b serve as the first imaging system.

The above-described embodiment describes that the X-ray diagnostic apparatus 1 is a biplane X-ray diagnostic apparatus including the first imaging system and the second imaging system; however, the embodiments are not limited thereto. For example, the X-ray diagnostic apparatus may include a single imaging system and, by moving the imaging system, acquire subtraction images that are generated over time in the first direction and the second direction.

The above-described embodiment describes the subtraction images that are generated by the subtraction circuitry 23 as exemplary blood vessel images; however, the embodiments are not limited thereto.

For example, the acquisition function 30a may acquire blood vessel images by using mechanical leaning. For example, first of all, the acquisition function 30a acquires multiple sets of leaning data consisting of combinations of subtraction images, each based on a contrast image and a mask image, and contrast images. The acquisition function 30a then generates a trained model that removes background components (bones and soft tissues) other than blood vessels on a contrast image by supervised leaning using leaning data where a contrast image serves as an input and a subtraction image serves as an output. The acquisition function 30a then inputs, to the trained model, a contrast image based on X-rays irradiated from the first direction and a contrast image based X-rays irradiated from the second direction. Accordingly, the acquisition function 30a removes the background components from each of the contest images and acquires a first blood vessel image based on the X-rays irradiated from the first direction and a second blood vessel image based on the X-rays irradiated from the second direction.

In another example, the acquisition function 30a generates an image corresponding to low-frequency components (soft tissues) in each of the contrast images by performing a low-frequency process on the contrast image based on the X-rays irradiated from the first direction and the contrast image based on the X-rays irradiated from the second direction. The acquisition function 30a performs subtraction between each of the contrast images and and an image obtained by performing the low-frequency process from each of the contest images to remove the low-frequency components other than high-frequency components (such as blood vessels) from each of the contrast images. Accordingly, the acquisition function 30a acquires the first blood vessel image based on the X-rays irradiated from the first direction and the second blood vessel image based on the X-rays irradiated from the second direction.

The word "processor" used in the descriptions given above refers to, for example, a central processing unit (CPU), a graphics processing unit (GPU) or a circuit, such as an application specific integrated circuit (ASIC) or a programmable logic device (for example, a simple programmable logic device (SPLD), a complex programmable logic device (CPLD) or a field programmable gate array (FPGA)). The processor implements functions by reading and executing a program that is saved in a storage circuit. Instead of saving the program in the storage circuit, the processor may be configured to have a circuit in which the program is directly incorporated. In this case, the processor implements the functions by reading and executing the program that is incorporated in the circuit. Each processor of the embodiment is not limited to the case where each processor is configured as a single circuit, and multiple independent circuits may be combined into one processor to implement the functions. Furthermore, the multiple components illustrated in FIG. 1 may be integrated into a single processor and implement the functions.

The content of the illustration in FIG. 1 is an example only. For example, FIG. 1 exemplifies multiple circuits (processors) including the subtraction circuitry 23, the filtering circuitry 24, the three-dimensional image processing circuitry 25, the imaging control circuitry the LUT 27, the affine transformation circuitry 28, the three-dimensional reconstruction circuitry 29, and the processing circuitry 30; however, the circuits are not necessarily configured independently. For example, given circuits among the circuits may be configured in a combined manner.

In the descriptions of the above-described embodiments, each of the components of each of the devices illustrated in the drawings is a functional idea and thus is not necessarily configured physically as unillustrated in the drawings. In other words, specific modes of distribution and integration of the devices are not limited to those illustrated in the drawings, and all or part of the devices may be configured in a distributed or integrated manner functionally or physically in any unit according to various types of loads and the situation in which the devices are used. Furthermore, all or part of the processing functions performed by the devices may be implemented by a CPU and a program that is analyzed and executed by the CPU or may be implemented as hardware based on a wired logic.

Furthermore, it is possible to implement the method of reconstructing a three-dimensional blood vessel image described in the above-described embodiment by executing a control program, which is prepared in advance, with a computer, such as a personal computer or a work station. The control program may be distributed via a network, such as the Internet. The control program may be stored in a computer-readable recording medium, such as a hard disk, a flexible disk (FD), a CD-ROM, a MO or a DVD, and may be read by the computer from the recording medium and thus executed.

The cases where the method of reconstructing a three-dimensional blood vessel image described in the first embodiment, the modification of the first embodiment and the second embodiment have been described above; however, the embodiments are not limited thereto. For example, the method of reconstructing a three-dimensional blood vessel image described in the first embodiment, the modification of the first embodiment and the second embodiment may be executed in the medical image processing apparatus that acquires blood vessel image from the X-ray diagnostic apparatus 1.

According to at least any one of the above-described embodiments, it is possible to easily reconstruct three-dimensional image data.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising processing circuitry configured to
   acquire a first blood vessel image based on X-rays that are irradiated from a first direction and a second blood vessel image based on X-rays that are irradiated from a second direction;
   determine a corresponding point on the second blood vessel image, which is a point corresponding to a subject point on the first blood vessel image, by using an epipolar line corresponding to the subject point and blood-flow information based on a change of a density of a contrast agent over time at the subject point; and
reconstruct a three-dimensional blood vessel image by using information about the subject point and the corresponding point.

2. The medical image processing apparatus according to claim 1, wherein the processing circuitry is configured to determine a set of subject points on the first blood vessel image as a center line and determine corresponding points on the second blood vessel image, which are points corresponding respectively to the subject points, by using epipolar lines corresponding respectively to the subject points and changes of the density of the contrast agent over time respectively at the subject points and the corresponding points, and
further reconstruct a three-dimensional center line by using information about the subject points and the corresponding points.

3. The medical image processing apparatus according to claim 1, wherein the processing circuitry is configured to determine, on the second blood vessel image, the epipolar line corresponding to the subject point on a blood vessel that is specified on the first blood vessel image and determine, on a blood vessel intersecting with the epipolar line, a corresponding point whose corresponding blood-flow information based on the change of the density of the contrast agent over time is similar to that at the subject point.

4. The medical image processing apparatus according to claim 1, wherein the processing circuitry is configured to determine, on the second blood vessel image, possible points whose corresponding blood-flow information is similar to that about the subject point on the blood vessel specified on the first blood vessel image and determine, as the corresponding point, a possible point intersecting with the epipolar line corresponding to the subject point from among the possible points.

5. The medical image processing apparatus according to claim 1, wherein the processing circuitry is configured to perform, as a pre-process, calculation of the blood-flow information about all the pixels in blood vessels on the second blood vessel image.

6. The medical image processing apparatus according to claim 1, wherein the processing circuitry is configured to calculate a blood inflow time as the blood-flow information.

7. The medical image processing apparatus according to claim 1, wherein the processing circuitry is configured to determine the corresponding point by further using continuity of blood vessel as a constraint condition.

8. The medical image processing apparatus according to claim 1, wherein the processing circuitry is configured to determine a size of a blood vessel on the basis of a width of the blood vessel at the corresponding point and reconstruct the three-dimensional blood vessel image.

9. The medical image processing apparatus according to claim 8, wherein the processing circuitry is configured to determine a magnifying factor from a set of coordinates of the blood vessel that is determined on the basis of the corresponding point and correct the size of the blood vessel by using the magnifying factor.

10. A reconstruction method comprising:
acquiring a first blood vessel image based on X-rays that are irradiated from a first direction and a second blood vessel image based on X-rays that are irradiated from a second direction;
determining a corresponding point on the second blood vessel image, which is a point corresponding to a subject point on the first blood vessel image, by using an epipolar line corresponding to the subject point and blood-flow information based on a change of a density of a contrast agent over time at the subject point; and
reconstructing a three-dimensional blood vessel image by using information about the subject point and the corresponding point.

11. The reconstruction method according to claim 10, further comprising:
determining a set of subject points on the first blood vessel image as a center line and determining corresponding points on the second blood vessel image, which are points corresponding respectively to the subject points, by using epipolar lines corresponding respectively to the subject points and changes of the density of the contrast agent over time respectively at the subject points and the corresponding points, and
further reconstructing a three-dimensional center line by using information about the subject points and the corresponding points.

12. The reconstruction method according to claim 10, further comprising determining, on the second blood vessel image, the epipolar line corresponding to the subject point on a blood vessel that is specified on the first blood vessel image and determining, on a blood vessel intersecting with the epipolar line, a corresponding point whose corresponding blood-flow information based on the change of the density of the contrast agent over time is similar to that at the subject point.

13. The reconstruction method according to claim 10, further comprising determining, on the second blood vessel image, possible points whose corresponding blood-flow information is similar to that about the subject point on the blood vessel specified on the first blood vessel image and determining, as the corresponding point, a possible point intersecting with the epipolar line corresponding to the subject point from among the possible points.

14. The reconstruction method according to claim 1, further comprising performing, as a pre-process, calculation of the blood-flow information about all the pixels in blood vessels on the second blood vessel image.

15. The reconstruction method according to claim 10, further comprising calculating a blood inflow time as the blood-flow information.

16. The reconstruction method according to claim 10, further comprising determining the corresponding point by further using continuity of blood vessel as a constraint condition.

17. The reconstruction method according to claim 10, further comprising determining a size of a blood vessel on the basis of a width of the blood vessel at the corresponding point and reconstructing the three-dimensional blood vessel image.

18. The reconstruction method according to claim 17, further comprising determining a magnifying factor from a set of coordinates of the blood vessel that is determined on the basis of the corresponding point and correcting the size of the blood vessel by using the magnifying factor.

19. An X-ray diagnostic apparatus comprising:
an X-ray tube that irradiates X-rays from a first direction and a second direction; and
processing circuitry configured to
acquire a first blood vessel image based on the X-rays that are irradiated from the first direction and a second blood vessel image based on the X-rays that are irradiated from the second direction;
determine a corresponding point on the second blood vessel image, which is a point corresponding to a subject point on the first blood vessel image, by using an epipolar line corresponding to the subject point and blood-flow information based on a change of a density of a contrast agent over time at the subject point; and
reconstruct a three-dimensional blood vessel image by using information about the subject point and the corresponding point.

* * * * *